United States Patent
Hiseni et al.

(10) Patent No.: US 10,196,630 B2
(45) Date of Patent: Feb. 5, 2019

(54) IMMOBILIZED PROLINE-SPECIFIC ENDOPROTEASE

(71) Applicant: DSM IP ASSETS B.V., Heerlen (NL)

(72) Inventors: Aida Hiseni, Echt (NL); Igor Galaev, Echt (NL); Luppo Edens, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 252 days.

(21) Appl. No.: 14/893,186

(22) PCT Filed: Jun. 2, 2014

(86) PCT No.: PCT/EP2014/061305
§ 371 (c)(1),
(2) Date: Nov. 23, 2015

(87) PCT Pub. No.: WO2014/191571
PCT Pub. Date: Dec. 4, 2014

(65) Prior Publication Data
US 2016/0102300 A1 Apr. 14, 2016

(30) Foreign Application Priority Data

May 31, 2013 (EP) .................................. 13170062

(51) Int. Cl.
| | | |
|---|---|---|
| *C12C 11/11* | (2006.01) | |
| *C12N 11/08* | (2006.01) | |
| *C12P 21/00* | (2006.01) | |
| *C12N 9/62* | (2006.01) | |

(Continued)

(52) U.S. Cl.
CPC ............. *C12N 11/08* (2013.01); *C12C 5/004* (2013.01); *C12C 11/11* (2013.01); *C12N 9/62* (2013.01); *C12N 11/06* (2013.01); *C12Y 304/21026* (2013.01)

(58) Field of Classification Search
None
See application file for complete search history.

(56) References Cited

FOREIGN PATENT DOCUMENTS

| WO | 2002046381 A2 | 6/2002 |
|---|---|---|
| WO | 03104382 A1 | 12/2003 |
| WO | 2005027953 A2 | 3/2005 |

OTHER PUBLICATIONS

Cantone ("Efficient immobilization of industrial biocatalysts: criteria and constraints for the selection of organic polymeric carries and immobilization methods" Chemical Society Review, 2013, 42, 6262-6276 and supplemental information, published Mar. 25, 2013,) (Year: 2013).*

(Continued)

*Primary Examiner* — Robert J Yamasaki
*Assistant Examiner* — Charles Zoltan Constantine
(74) *Attorney, Agent, or Firm* — McBee Moore Woodward & Vanik IP, LLC; Susan McBee; Chester Moore

(57) ABSTRACT

The present invention relates to immobilized proline-specific endoprotease, wherein the proline-specific endoprotease is immobilized on a carrier comprising methacrylate which has been functionalized with amino dimethylene, and wherein the carrier has a particle size range of 100 to 400 μm. The invention also relates to a process for producing beer comprising the steps of preparing a mash, fermenting the beer, and stabilizing the beer, wherein the beer is incubated with the immobilized proline-specific endoprotease.

17 Claims, 2 Drawing Sheets

(51) Int. Cl.
*C12C 5/00* (2006.01)
*C12N 11/06* (2006.01)

(56) References Cited

OTHER PUBLICATIONS

Purolite ECR ("Purolite ECR: Enzyme Immobilization Resins & Kits", Polysciences, Warrington PA, 2013) (Year: 2013).*
"c-LEcta and Purolite clllaborate to market Calb Immo Plus immobilized enzyme", Focus on Catalysts, Jun. 1, 2014, vol. 2014, No. 9.
International Search Report from corresponding PCT/EP2014/061305, dated Jul. 30, 2014.
Guisan, "Immobilization of Enzymes and Cells", Second Edition, Humana Press, 2006, 13 pages.

* cited by examiner

IMMOBILIZED PROLINE-SPECIFIC ENDOPROTEASE

CROSS REFERENCE TO RELATED APPLICATIONS

This application is a § 371 National Stage Application of PCT/EP2014/061305, filed 2 Jun. 2014, which claims priority to EP 13170062.7, filed 31 May 2013.

BACKGROUND

Field of the Invention

The present invention relates to immobilized proline-specific endoprotease and a process for preparing beer wherein the immobilized proline-specific endoprotease is used.

Description of Related Art

Proline-specific endoproteases are enzymes that can be derived from bacteria and fungi, for instance proline specific endoprotease from *Aspergillus niger* as disclosed in WO2002/046381. Proline-specific endoprotease are capable of cleaving a protein at places where the protein contains a prolyl-residue in its chain. WO2002/046381 discloses that such proline-specific endoprotease can be used for reducing haze in a beverage such as beer. Haze in beer consists mainly of protein-polyphenol aggregates. To reduce haze, the proline-specific endoprotease can be added to the wort, during fermentation or during a stabilization phase of beer.

WO2005/027953 discloses that proline-specific endoprotease reduced the gluten levels in beer when proline-specific endoprotease was added during mashing or fermentation of the beer.

In order to be able to reuse the proline-specific endoprotease in for instance a beer production process, it was suggested in WO2003/104382 to immobilize the enzyme and to minimize the risk that the enzyme remains present in the final product.

Immobilization of enzymes is known since decades (see "Immobilization of Enzyme and Cells", Second Edition, edited by Jose M. Guisan, 2006, Humana Press Inc.). The most common procedures of enzyme immobilization are covalent coupling, entrapment, micro-encapsulation and cross-linking.

However, no suitable immobilization for proline-specific endoprotease has been disclosed wherein the enzyme remains active on partially or entirely insoluble substrates, such as haze forming protein-polyphenol aggregates in beer, or gluten.

The aim of the present invention is an immobilized proline-specific endoprotease which is sufficiently active on insoluble substrates.

SUMMARY

The present disclosure relates to immobilized proline-specific endoprotease immobilized on a carrier comprising aminofunctionalized methacrylate having a particle size range of 100 to 400 μm. Surprisingly, it was found that immobilized proline-specific endoprotease as disclosed herein not only remained its enzymatic activity on a large substrate such as gluten, but also showed a higher relative activity at a lower temperature as compared to the relative activity of free enzyme at this lower temperature.

The present disclosure also relates to a process for producing immobilized proline-specific endoprotease, comprising activating the amino group in an amino-functionalized methacrylate carrier with a bifunctional crosslinking agent, immobilizing the proline-specific endoprotease on the amino-functionalized methacrylate carrier at an enzyme: carrier ratio of 0.01-0.07 w/w, and producing the immobilized proline-specific endoprotease.

The present disclosure also relates to a process for producing beer, comprising preparing a mash, fermenting the beer, and stabilizing the beer, wherein the beer is incubated with immobilized proline-specific endoprotease.

DETAILED DESCRIPTION OF A PREFERRED EMBODIMENT

Figure 1:
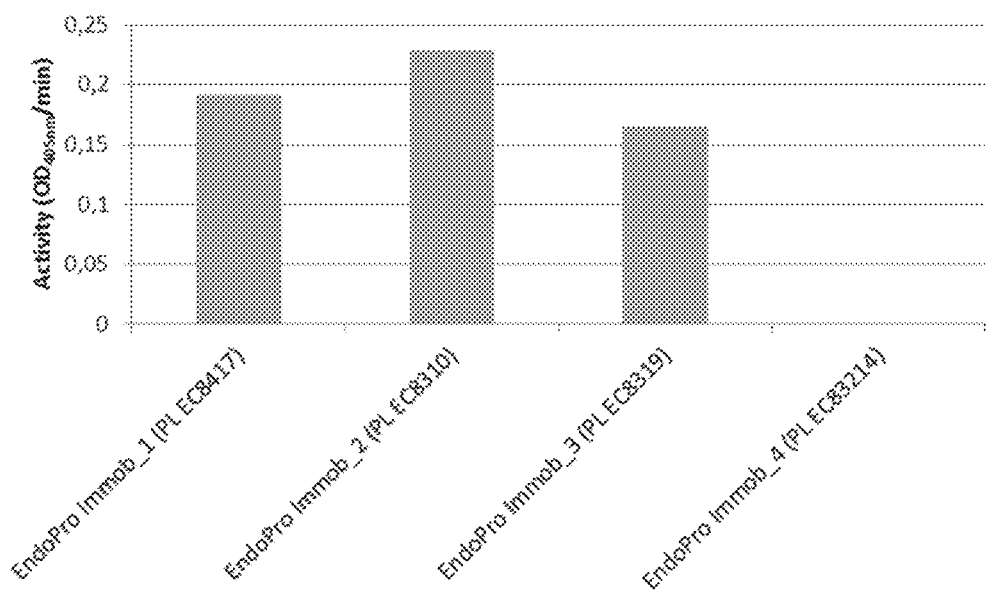
FIGS. 1-3 depict embodiments of the disclosure described herein.

Disclosed herein is an immobilized proline-specific endoprotease immobilized on a carrier comprising amino-functionalized methacrylate polymer. Preferably the immobilized proline-specific endoprotease has a particle size range of 100 to 400 μm. Preferably, the carrier comprising amino-functionalized methacrylate polymer may have a particle size range of between 150 to 350 μm. Preferably, the methacrylate polymer has been amino-functionalized with dimethylene.

Advantageously an immobilized proline-specific endoprotease as disclosed herein is immobilized on a carrier which has a pore size distribution d50 of 1500-2100 Å, for instance a pore size distribution d50 of 1600 to 2000 Å. The pore size distribution d50 is a known term to a skilled person in the art, and is defined as the value of the pore diameter at 50% in the cumulative distribution.

Usually, the amino-functionalized methacrylate carrier for immobilizing proline-specific endoprotease has a surface area larger than 40 $m^2/g$, such as larger than 45 $m^2/g$, or larger than 50 $m^2/g$. The methacrylate carrier for immobilizing proline-specific endoprotease usually has a moisture retention of 58 to 70%, such as 60 to 68%, or 62 to 66%. Moisture retention is defined herein as the ratio between the weight of the completely hydrated carrier and the weight of the completely dried carrier.

Surprisingly, it was found that a proline-specific endoprotease immobilized on a carrier as disclosed herein remains not only active on large polymeric and/or protein-polyphenol aggregated substrates such as haze, for instance beer haze but was also able to hydrolyse gluten, such as barley gluten.

An enzyme having proline-specific endoprotease activity that is immobilized on a carrier as disclosed herein may be any suitable enzyme capable of cleaving a peptide or protein at places where the protein or peptide contains a prolyl-residue in its chain. A proline-specific endoprotease may be derived from bacterial or fungal origin, such as from the genus *Flavobacterium, Sphingomonas, Aeromonas, Xanthomonas, Bacteroides, Aspergillus* or *Penicillium*, for instance from *Flavobacterium meningosepticum, Sphingomonas capsulata, Aspergillus niger* or *Penicillium chrysogenum*. A proline-specific endoprotease as disclosed herein belongs to enzyme classification EC 3.4.21.26. A proline-specific endoprotease is preferably an enzyme that hydrolyses a peptide bond at the carboxy-terminal end of proline residues, resulting in a peptide and/or polypeptide fragment with a C-terminal proline.

The wording immobilized is used herein to indicate that an enzyme is attached to a carrier, such as a methacrylate carrier. Immobilization of an enzyme can be achieved by adsorption, entrapment or cross-linking of the enzyme on or to the carrier, which is known to a skilled person in the art (see "Immobilization of Enzyme and Cells", Second Edition, edited by Jose M. Guisan, 2006, Humana Press Inc).

The present disclosure provides a proline-specific endoprotease immobilized by cross-linking on a methacrylate carrier.

In one embodiment the present disclosure relates to a process for producing immobilized proline-specific endoprotease as disclosed herein, comprising activating the amino group in an amino-functionalized methacrylate carrier with a bifunctional crosslinking agent, immobilizing the proline-specific endoprotease on the carrier and producing the immobilized proline-specific endoprotease.

Surprisingly, it was found that using a process for immobilizing proline-specific endoprotease as disclosed herein results in an immobilized proline-specific endoprotease which has a higher relative activity at a lower temperature as compared to the relative activity of the free enzyme.

The methacrylate carrier may be amino functionalized with for instance a dimethylene or a hexamethylene spacer, preferably an dimethylene spacer.

Activation of the amino group in amino-functionalized methacrylate by a bifunctional crosslinking agent results in immobilization of the enzyme to the carrier. Preferably, the cross-linking agent is glutaraldehyde. Activation of the amino-group with glutaraldehyde may be performed in any suitable way which is known to a skilled person the art.

During the process for immobilization of the enzyme to the carrier, any suitable enzyme:carrier ratio may be applied such as a ratio of 0.01-0.07 w/w, or a ratio enzyme:carrier of 0.02 to 0.06 w/w, or an enzyme:carrier ratio of 0.03 to 0.05 w/w. It was found that at the indicated enzyme:carrier ratio in a process for immobilization as disclosed herein an immobilized proline-specific endoprotease on a methacrylate carrier with comparable activity as the free enzyme was obtained.

Preferably, a process for immobilizing proline-specific endoprotease as disclosed herein is performed at temperature of 10 to 50° C., such as between 15 and 40° C., such as at a temperature of between 20 and 30° C.

A process for immobilizing proline-specific endoprotease as disclosed herein may be performed at any suitable pH, such as a pH of between 6 to 8, or a pH between 6.5 and 7.5. Any buffer to maintain the pH at a desirable level may be used, for instance a buffer having a salt concentration of between 20 and 150 mM, or between 40 and 120 mM, or between 60 and 100 mM, such as between 70 and 90 mM. A suitable buffer may for instance be a phosphate buffer.

A process for immobilizing proline-specific endoprotease as disclosed herein may be performed during 4 to 48 hrs, such as between 8 and 36 hrs, or between 10 and 24 hrs.

In one embodiment the present disclosure relates to the use of immobilized proline-specific endoprotease as disclosed herein for the hydrolysis of gluten, such as barley gluten.

Gluten is a group of proline- and glutamine-rich proteins that is found in wheat, rye, barley and oat, which can be subdivided into glutenins and prolamines. Only the prolamine-fraction of gluten gives rise to allergic reactions to gluten intolerant people, and/or to people suffering from Celiac disease. Prolamines in the different cereals are commonly indicated as gliadin in wheat, hordein in barley, secalin in rye, and avenin in oats. For the purpose of the present disclosure the wording gliadin can be used to indicate the prolamine fraction of all different cereals.

In another embodiment the present disclosure relates to a process for producing beer comprising preparing a mash, fermenting the beer, and stabilizing the beer, wherein the beer is incubated with immobilized proline-specific endoprotease as disclosed herein.

Beer is used herein to indicate a liquid during any stage in the beer production process. Beer may be or may not be a liquid ready for consumption. The wording beer also comprises wort or green beer.

There are many different processes for producing beer, which are known to a skilled person in the art. Usually a beer brewing process comprises milling and mashing cereals, such as barley, and the resulting mash is filtered to give wort. The wort is then boiled to inactivate all residual enzymatic activities and subsequently the wort is inoculated with yeast. Fermenting beer in a process according to the present disclosure comprises inoculating the wort with yeast and incubating the yeast in the wort to ferment available sugars into alcohol. This fermentation is also called the primary fermentation. The "green" beer resulting from this primary fermentation still contains some non-settled yeasts as well as relatively high levels of undesirable flavor components, notably diketones, such as diacetyl and acetyl aldehyde.

The primary fermentation is followed by a maturation phase, also called the secondary fermentation. Fermenting beer in a process as disclosed herein may comprise a primary and a secondary fermentation. The maturation phase is intended to convert the undesirable flavour components such as diketones into better tasting components.

After maturation, the beer is stabilized. The stabilization phase is intended to promote formation of polyphenol-protein aggregates and enables their precipitation. Surprisingly it was found that when beer was incubated with immobilized proline-specific endoprotease as disclosed herein the formation of polyphenol-protein aggregates was reduced or prevented. In addition it was found that when beer was incubated with immobilized proline-specific endoprotease as disclosed herein, the gluten (gliadin) content in beer was reduced.

Accordingly, in one embodiment the present disclosure relates to a process for reducing the gluten in beer, comprising incubating beer with immobilized proline specific endoprotease, wherein the immobilized proline specific endoprotease hydrolyses at least part of gluten present in the beer, and reducing gluten in beer. Accordingly, incubating immobilized proline-specific endoprotease in a process for producing beer comprises hydrolyzing gluten.

Incubating beer with immobilized proline-specific endoprotease may be performed at any suitable phase during a beer production process. Preferably, incubating beer with immobilized proline-specific endoprotease is performed during a phase wherein the beer is a clear liquid. For instance, a process for producing beer comprises incubating immobilized proline-specific endoprotease during or after the stabilization phase. However, the immobilized proline-specific endoprotease may also be added during any other phase in the beer brewing process and prevent or reduce the formation of haze, and/or hydrolyse gluten into non-toxic fragments. As used herein, hydrolysing gluten into non-toxic fragments, means that the gliadin fraction of gluten is hydrolysed.

Preferably, incubating immobilized proline-specific endoprotease in a process for producing beer is performed at a temperature of between −1 and 20° C., such as a temperature of between 0 and 15° C., or a temperature of between 1 and 10° C., or a temperature of between 2 and 8° C. Surprisingly, it was found that immobilized proline-specific endoprotease was able to hydrolyse gluten and reduce haze in beer at these low temperatures.

Incubating beer with immobilized proline-specific endoprotease may be performed in batch mode or in continuous mode. When incubating proline-specific endoprotease is performed in continuous mode, immobilized proline-specific endoprotease may be packed in a column which retains the immobilized proline-specific endoprotease and allows the beer to flow through the column. A suitable column may comprise a sieve at the top and at the bottom of the column. Depending on the amount of insoluble material in the beer, immobilized proline-specific endoprotease may be packed in a fluidized bed column or a packed bed column. The preparation of such column is known to a skilled person in the art. Preferably, beer is a clear liquid when brought into contact with immobilized proline-specific endoprotease.

After stabilization the beer can be packaged in a bottle, can or a keg. In another embodiment the present disclosure relates to the use of immobilized proline-specific endoprotease for the hydrolysis of gluten. Preferably, the immobilized proline-specific endoprotease is used in a process for producing beer.

FIGURES

FIG. 1. Enzyme activity of EndoPro immobilized on different carriers determined with Ac-AAP-pNA substrate. The activity of the enzyme is determined as the increase of absorbance at 405 nm in time (OD 405 nm/min).

Figure 2:
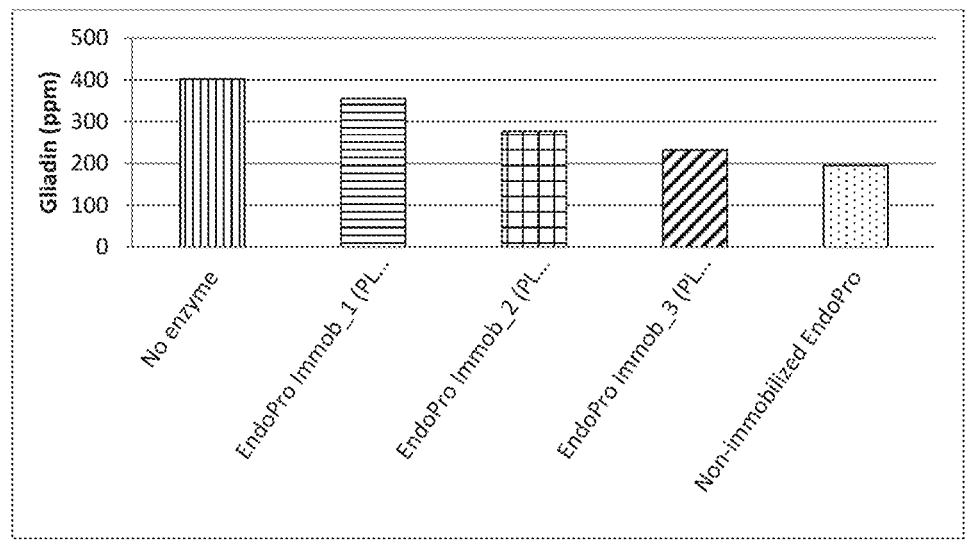

FIG. 2. Gliadin reduction in wort using immobilized and non-immobilized EndoPro.

Figure 3:
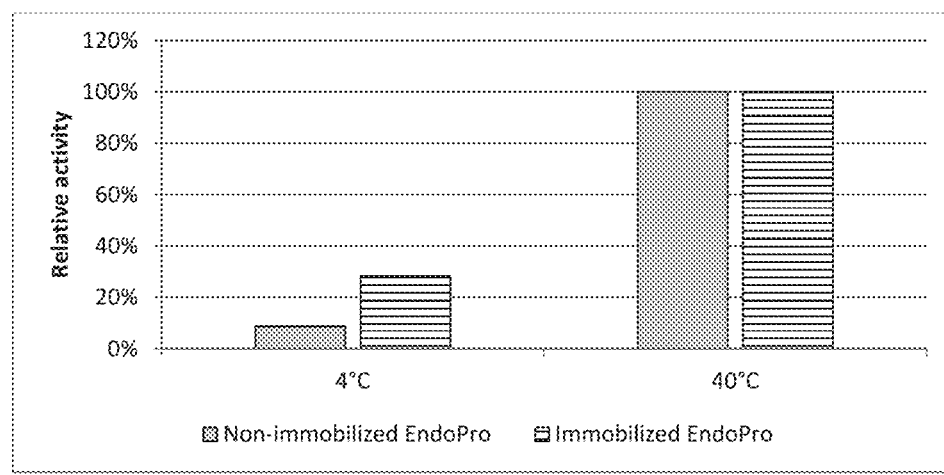

FIG. 3. Relative activity of immobilized and non-immobilized EndoPro at 4° C. compared to the activity at 40° C. (optimal temperature).

EXAMPLES

Materials and Methods

Proline-Specific Endoprotease (EndoPro)

*Aspergillus niger* proline-specific endoprotease (EndoPro), was produced by fermenting an *A. niger* strain containing the gene encoding proline-specific endoprotease (GI: 21725363; protein accession no: AX458699) by known methods in the art. The fermentation broth obtained after fermentation of an *Aspergillus niger* strain was further submitted to ultrafiltration. The prolyl-specific activity in the final EndoPro sample was 12.4 PPU/ml, and determined using a 2 mM N-carbobenzoxy-glycine-proline-p-nitroanilide (Z-Gly-Pro-pNA) in 0.1 M citric acid/0.2 M disodium phosphate buffer pH 4.6, containing 40% dioxan.

To 1 ml of this buffer pH 4.6, 250 µl of the substrate solution was added followed by 100 µl of the enzyme solution. The reaction mixture was incubated at 37° C. and the release of liberated pNA was measured spectrophotometrically at 405 nm using a Tecan Genios spectrophotometer. The activity is expressed as Proline Protease Units (PPU). One PPU is defined as the amount of enzyme required to release 1 µmol pNA from Z-Gly-Pro-pNA in 1 minute under the described assay conditions. To calculate the concentrations a molar extinction coefficient of 10500 $M^{-1}$ $cm^{-1}$ was used.

The protein concentration was estimated to be 146 mg/g determined using Kjeldahl.

Enzyme Carriers

Purolite ECR enzyme carriers were used for the immobilization of EndoPro. The main properties of the carriers are summarized in Table 1.

TABLE 1

| Purolite ® carrier properties | | | | | |
|---|---|---|---|---|---|
| Carrier name | Moisture retention (%) | Particle size range (µm) | Surface area ($m^2/g$) | d50, Meso and Macrospores (Å) | Spacer |
| Purolite ® ECR8310 | 58-62 | 150-300 | >70 | 850-1200 | dimethylene (C2) |
| Purolite ® ECR8319 | 62-66 | 150-300 | >50 | 1600-2000 | dimethylene (C2) |
| Purolite ® ECR8417 | 61-65 | 150-300 | >50 | 1600-2200 | hexamethylene (C6) |
| Purolite ® ECR8214 | 60-66 | 150-300 | >60 | 1200-1800 | epoxy |

Determination Total Nitrogen Determination

Total nitrogen (N) of the sample was determined using Kjeldahl (Bradstreet, Raymond B. "*The Kjeldahl method for organic nitrogen.*" (1965). The beads with the immobilized enzyme were dried prior to the measurement using the Mettler Tolodo HB43-S (Halogen). Protein was calculated using a conversion factor of 6.25*N.

Determination of the Gliadin Content in Wort

The gliadin content was determined as a measure for the gluten content. The analytical detection of gliadins in wort was determined with the RIDASCREEN® Gliadin competitive ELISA kit (R-Biopharm) according to the manufacturer's instructions. This method is based on the R5 antibody (Mendez), which is recommended by the Codex Alimentarius (CODEX STAN 118-1979). The limit of quantification is 5 ppm gliadin (=10 ppm gluten).

Generally, the gliadin content can be converted into gluten by multiplying the gliadin content with a factor 2. However, this value is not absolute as the gliadin fraction with respect to gluten can vary in the raw material (Diaz-Amigo & Popping, Journal of AOAC International, Vol. 95, No. 2, 2012).

Determination of the Gliadin Content in Beer

The analytical detection of gliadin in beer was determined with the RIDA® QUICK Gliadin kit (R-Biopharm) according to the manufacturer's instructions. This method is based on the R5 antibody (Mendez), which is recommended by the Codex Alimentarius (CODEX STAN 118-1979). The detection limit is 2.5 ppm gliadin (=5 ppm gluten).

Example 1. EndoPro Immobilization on Different Purolite® Carriers

Prior to EndoPro immobilization, the Purolite® carriers ECR8310, -8319 and -8417 were pre-activated with 2% glutaraldehyde (v/v) in 0.02M K-phosphate buffer, pH 8.0 for 1 h, followed by 3 times washing off the unreacted glutaraldehyde with the same buffer. The Purolite ECR8214 carrier did not require any activation. The ECR8214 beads were only washed 3 times with the same buffer and used as such. Finally, the beads were filtered using a glass filter and the semi-dry beads were stored until use. For immobilization, beads were mixed with buffer at a beads/buffer ratio of ¹/₁₀ (w/v) and soluble EndoPro was added to the beads/buffer mixture at an enzyme loading as shown in Table 2.

TABLE 2

Immobilization conditions. Potassium phosphate buffer was used

| Carrier name | Enzyme loading (mg/g carrier) | Molarity buffer (mM) | pH buffer |
|---|---|---|---|
| Purolite ® ECR8310 | 80 | 35 | 5.8 |
| Purolite ® ECR8319 | 50 | 84 | 7 |
| Purolite ® ECR8417 | 50 | 84 | 7 |
| Purolite ® ECR8214 | 21 | 35 | 5.8 |

After continuous overnight shaking at room temperature, the beads were washed 3 times with 0.1M NaOAc, pH 5.0. Finally, the beads containing immobilized EndoPro were suspended in the same buffer and stored at 4° C.

Example 2. Enzyme Activity of EndoPro Immobilized on 4 Different Purolite Carriers EndoPro activity was determined as OD405 nm/min using acetate-alanine-alanine-proline-p-nitroaniline (Ac-AAP-pNA) as substrate. The amount of liberated p-nitroaniline (pNA) formed in time is a measure of EndoPro activity and was determined spectrophotometrically at 405 nm using a Tecan GENios spectrophotometer.

Non-immobilized or immobilized Endopro immobilized on one of the 4 Purolite® carriers was added to 0.1 M NaOAc, pH 5.0, in a microtiter plate. Prior to the addition of 3 mM Ac-AAP-pNA (end concentration) stock in 0.1M NaOAc, pH 5.0, the enzyme was incubated at 40° C. for 5 min. Kinetic measurement was started and the activity calculated from the slope of the curve. The activity of the enzyme is determined as the increase of absorbance at 405 nm in time (OD 405 nm/min) as a result of liberated pNA from the substrate Ac-AAP-pNA.

FIG. 1 demonstrates that the Endopro immobilized on Purolite® carriers ECR8310, -8319 and -8417 showed activity. No activity was detected with EndoPro immobilized on Purolite® carrier ECR8214. Therefore, no further study of this particular preparation was performed.

Example 3. Removal of Gliadin from Wort by Using Immobilized Endopro

To test whether Endopro immobilized on Purolite® carriers ECR8310, -8319 and -8417 was also active on gluten, 0.05 mg of enzyme, immobilized and free EndoPro (control), respectively, were added to 10 ml wort (Research Brewery St. Johann, Train-St. Johann, Germany; Batch number: 4/2013) in a 15 ml reaction tube.

The mixtures were shaken overnight at room temperature. The following day, the gluten content in wort was determined by the process as described in methods. The results in FIG. 2 show the residual gliadin content in wort.

We found that immobilized EndoPro had the best activity towards large, protein substrate when immobilized on Purolite® ECR8319 carrier immobilized according to the process as described in Example 1, In comparison, when immobilized on the same carrier under different conditions (pH 8.2, molarity 35 mM, enzyme loading 80 mg/g carrier) only about half of the activity towards gluten was obtained (data not shown).

Example 4. Relative Activity of Immobilized and Free Endopro at 4° C. Compared to 40° C.

For the determination of the relative activity at 4° C. compared to the activity at 40° C. the non-immobilized and immobilized EndoPro Purolite® ECR8319 (preparation immobilized as described above) enzyme was added to 0.1 M NaOAc, pH 5.0 comprising 3 mM Ac-AAP-pNA in a total volume of 1 ml. The reaction mixtures were shaken at 900 rpm in a thermo-regulated mixer (Eppendorf). A supernatant sample was taken every minute and the reaction stopped with 0.5M HCl (sample/HCl ratio of 50/1 (v/v)). The absorbance at 405 nm was measured using the Tecan GENios spectrophotometer. The slopes (OD 405 nm/min) at 4° C. were compared to the slopes at the optimal activity temperature of 40° C. The absolute activity of immobilized Endopro was 0.53 and 1.85 OD 405 nm/min and of non-immobilized Endopro 0.06 and 0.65 OD 405 nm/min at 4° C. and 40° C., respectively. The activity at 40° C. was set at 100%.

FIG. 3 shows that the relative activity of immobilized EndoPro at 4° C. is 3 times higher than the relative activity of the non-immobilized EndoPro.

Example 5. Conversion of Gliadin in Beer by Immobilized EndoPro at 4 and 15° C.

Three different volumes (Table 3) of the immobilized EndoPro immobilized on Purolite® ECR8319 preparation as described in Example 1, were pipetted into 50 ml of beer (Research Brewery St. Johann, Train-St. Johann, Germany; Batch number: 42/2012). The mixtures were incubated at 4° C. and 15° C., respectively, on a roller-mixer. 1 ml beer samples were taken after 0, 5, 1, 19 and 24 hr. The residual gliadin in the samples was determined by the process as described in methods. The results are depicted in Table 3 and show the gliadin reduction in beer. Overall, the immobilized EndoPro is able to degrade gliadin in beer at a temperature of 4° C. to the same or similar extent as at 15° C. After 24 hours, gliadin was degraded in all samples to an undetectable limit (LOD 2.5 ppm). By using higher dosages of immobilized EndoPro (10 ml), the gliadin could be degraded to an undetectable limit even after 1 hour of incubation.

TABEL 3

Time-, dose- and temperature dependent gliadin removal from beer by immobilized EndoPro.

| | 4° C. | | | | 15° C. | | | |
|---|---|---|---|---|---|---|---|---|
| Time (h) | 0.5 | 1 | 19 | 24 | 0.5 | 1 | 19 | 24 |
| Enzyme (ml) | | | | | | | | |
| 0.25 | +++ | +++ | + | − | +++ | +++ | − | − |
| 2.5 | ++ | ++ | − | − | ++ | + | − | − |
| 10 | + | − | − | − | − | − | − | − |

The concentration of residual gliadin is indicated as follows: (+++) >>2.5 ppm gliadin, (++) >2.5 ppm, (+) ≤2.5 ppm, (−) no gliadin.

CONCLUSION

The results shown in Examples 1 to 5 show that immobilized proline-specific endoprotease according to the present invention can convert a complex substrate such as gluten.

The invention claimed is:

1. An immobilized proline-specific endoprotease, wherein the proline-specific endoprotease is immobilized on a carrier comprising methacrylate which has been functionalized with dimethylene and which has a pore size distribution d50 of 1500-2100 Å, and wherein the immobilized proline-specific endoprotease has higher relative proline-specific endoprotease activity against acetate-alanine-alanine-proline-p-nitroaniline (Ac-AAP-pNA) at a temperature between −1 and 15° C. as compared to the proline-specific endoprotease when it is not immobilized.

2. The immobilized proline-specific endoprotease according to claim 1, wherein the carrier has a particle size range of 100 to 400 µm.

3. The immobilized proline-specific endoprotease according to claim 1, wherein the carrier has a pore size distribution d50 of 1600-2000 Å.

4. The immobilized proline-specific endoprotease according to claim 1, wherein said proline-specific endoprotease is from *Aspergillus*.

5. The immobilized proline-specific endoprotease according to claim 1, wherein said proline-specific endoprotease is from *Aspergillus niger*.

6. The immobilized proline-specific endoprotease of claim 1, wherein the higher relative proline-specific endoprotease activity is at a temperature between 1 and 10° C.

7. The immobilized proline-specific endoprotease of claim 1, wherein the higher relative proline-specific endoprotease activity is at a temperature between 2 and 8° C.

8. A process for producing the immobilized proline-specific endoprotease according to claim 1, comprising activating an amino group in an amino-functionalized methacrylate carrier with a bifunctional crosslinking agent, immobilizing the proline-specific endoprotease on the carrier and producing the immobilized proline-specific endoprotease, wherein the amino-functionalized methacrylate carrier has a pore size distribution d50 of 1500-2100 Å.

9. The process according to claim 8, wherein the proline-specific endoprotease is immobilized on the carrier at an enzyme:carrier ratio of 0.01-0.07 w/w.

10. The process according to claim 8, wherein the bifunctional crosslinking agent is glutaraldehyde.

11. The process according to claim 8, wherein the immobilizing is performed at a temperature of between 10 to 50° C.

12. The process according to claim 8, wherein the immobilizing is performed at a pH of 6 to 8.

13. The process according to claim 8, wherein the immobilizing is performed between 4 to 48 hrs.

14. A process for producing beer comprising
a. preparing a mash;
b. fermenting the beer; and
c. stabilizing the beer;
wherein the beer is incubated with the immobilized proline-specific endoprotease according to claim 1.

15. The process according to claim 14, wherein the immobilized proline-specific endoprotease is incubated during or after stabilizing the beer.

16. The process according to claim 14, wherein said incubation is performed at a temperature of between 0 and 15° C.

17. The process according to claim 14, wherein said incubating comprises hydrolysing gluten.

* * * * *